Figure 1A:
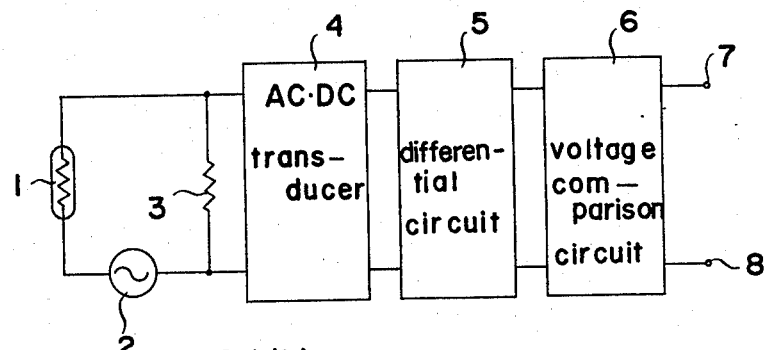

United States Patent [19]

Terada et al.

[11] 4,270,085
[45] May 26, 1981

[54] HUMIDITY DETECTING APPARATUS

[75] Inventors: Jiro Terada; Tsuneharu Nitta, both of Katano; Yukihiko Ise, Toyonaka, all of Japan

[73] Assignee: Matsushita Electric Industrial Co. Ltd., Kadoma, Japan

[21] Appl. No.: 83,933

[22] Filed: Oct. 11, 1979

[30] Foreign Application Priority Data

Oct. 11, 1978 [JP] Japan .................................. 53-125339

[51] Int. Cl.³ ............................................ G01R 27/02
[52] U.S. Cl. .................................. 324/65 R; 73/336.5; 204/195 W
[58] Field of Search ............... 324/65 R, 71 R; 73/73, 73/336.5; 204/195 W

[56] References Cited

U.S. PATENT DOCUMENTS 2,663,190   12/1953   Ilgenfritz .............................. 73/336.5

Primary Examiner—Stanley T. Krawczewicz
Attorney, Agent, or Firm—Wenderoth, Lind & Ponack

[57] ABSTRACT

This invention is directed to an apparatus capable of stably detecting humidity. More particularly, to stably detect the humidity in the atmosphere where temperature, relative humidity or wind flow vary, this humidity detecting apparatus converts the resistance variation, due to humidity, of a humidity-sensing resistor into voltage variation to draw out the voltage variation thereby to differentiate the voltage variation with a differential circuit and thereafter to compare the differentiation output with a set value. Therefore, the steam leakage from the high pressure, high temperature steam supply pipe or the relative humidity inside a microwave oven can be easily, automatically detected.

4 Claims, 9 Drawing Figures

HUMIDITY DETECTING APPARATUS

The present invention relates to a humidity detecting apparatus and, more particularly, to an apparatus which is capable of stably detecting humidity.

Conventionally it was extremely difficult to detect the humidity in the atmosphere where temperature, humidity, wind amount or the like were constantly being varied. In the detecting operation of the steam leakage from a system of high pressure, high temperature steam supply pipes where heating steam passes, the detection of the humidity becomes unstable, thus making it impossible to make the stable humidity detection, since the steam leakage condition constantly varies due to the temperature, humidity, air flow or the like around the location to be detected. This is because the base line of the detection temperature varies as the humidity condition constantly varies. Also, the relative humidity varies due to temperature, pressure or the like. Accordingly, it was extremely difficult to detect the steam leakage by the conventional humidity detecting apparatus.

Also, in the recent years, food cookers are automated. Among the microwave ovens, an oven is developed which detects the water content coming from the food during the heating operation to automatically stop the heating operation. The conventional automatic microwave oven is adapted to normally detect the relative humidity inside the oven chamber and to suspend the current flowing to the magnetron when the relative humidity has reached to a given value thereby to finish the heating operation of the food. Since the initial humidity inside the oven chamber differs depending upon many conditions such as date, time, temperature, air flow or the like, the conventional oven is adapted in its humidity detection circuit not to give influences upon the humidity detecting operation even if such many conditions as described hereinabove vary. However, in this case, the humidity detecting circuit becomes complex in construction and high cost in production.

Therefore, an object of the present invention is to provide a humidity detecting apparatus, wherein the stable humidity detection can be ensured even if the temperature, humidity, air flow or the like are varied in a location to be humidity-detected.

Another object of the present invention is to provide a humidity detecting apparatus, which can eliminate the disadvantages inherent in the conventional humidity detecting circuit, and which is simply in construction, easily in design and cheaper in production.

According to the present invention, there is provided a humidity detecting apparatus comprising a humidity-sensing resistor and a differential circuit for differentiating the voltage variation accompanied by the resistance variation of the humidity-sensing resistor thereby to detect variations in the surrounding humidity of said humidity-sensing resistor. In the preferred embodiment of the present invention, the humidity-sensing resistor is a metal oxide ceramic humidity-sensing resistor, and the time constant of the differential circuit is set within the range of 0.1 to 20 (seconds) to make it posssible to detect the humidity leakage. Furthermore, in the humidity detecting apparatus of the present invention, the humidity-sensing resistor is a ceramic, with an electrode attached thereto, of at least one oxide selected from among $Cr_2O_3$, $Fe_2O_3$, NiO, ZnO, $SnO_2$, $TiO_2$, $Al_2O_3$, MgO, $In_2O_3$, $MnO_2$, CuO, CoO, $MgCr_2O_4$, $FeCr_2O_4$, $NiCr_2O_4$, $MnCr_2O_4$, $CuCr_2O_4$, $CoCr_2O_4$, $Zn_2TiO_4$, $Zn_2SnO_4$, $Mg_2TiO_4$ and $Mg_2SnO_4$.

Figure 1B:
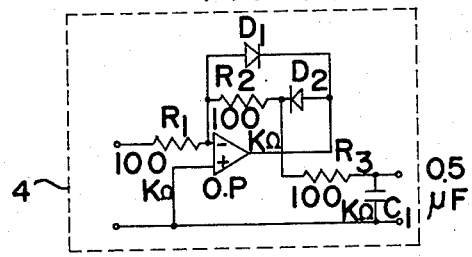
Figure 1C:
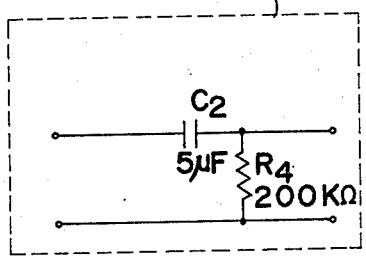
Figure 1D:
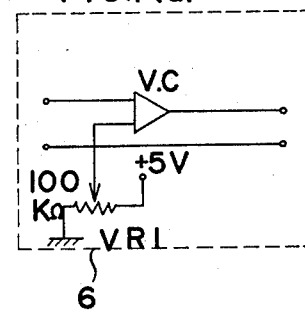
Figure 2:
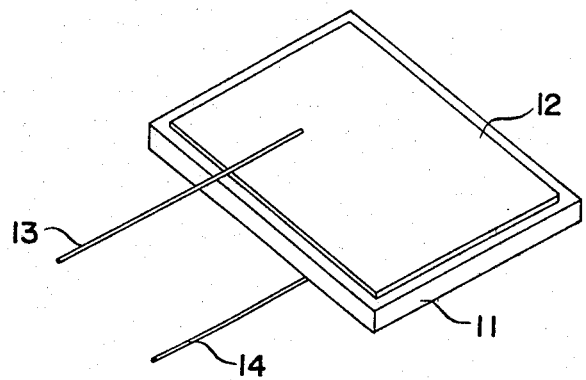
Figure 3:
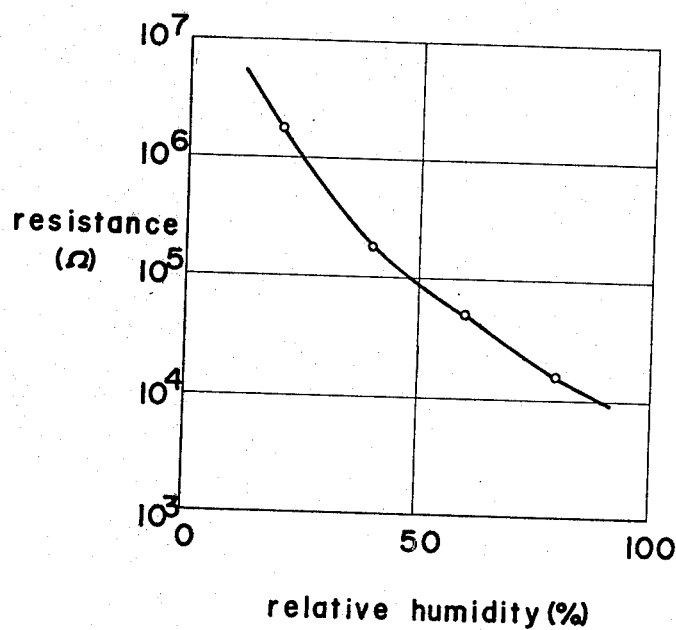
Figure 4A:
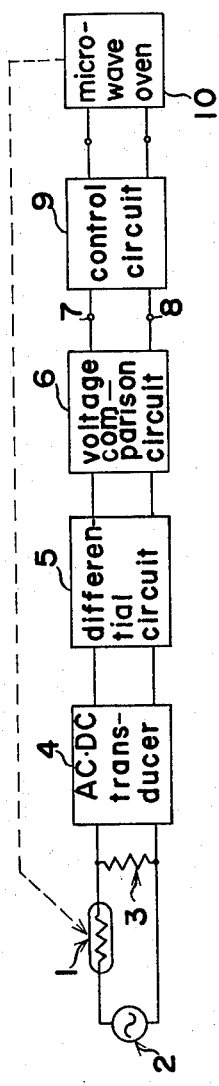
Figure 4C:
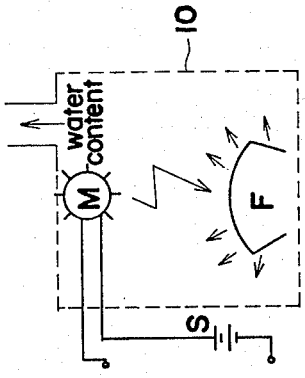

These objects and other objects and features, of the present invention will become more apparent from the following detailed description of the present invention when taken in conjunction with the accompanying drawings, in which FIGS. 1, (a) to (d), is a circuit diagram showing the construction of one embodiment of a humidity detecting apparatus including a humidity-sensing resistor of the present invention, FIG. 2 is a perspective view showing one example of the humidity-sensing resistor, FIG. 3 is a graph showing a typical relative humidity to resistance characteristics of the humidity-sensing resistor, and FIGS. 4, (a) to (c), shows one example of a circuit diagram of the humidity detecting apparatus where the present invention has been applied to a microwave oven.

Before proceeding the description, it is to be noted that like parts are designated by same numerals throughout the drawings.

Referring to FIG. 1, a humidity-sensing resistor 1, an oscillator 2 and a resistor 3 are connected in series to constitute a closed circuit. An AC-DC transducer 4 is adapted to convert the voltage, between terminals, of the resistor 3 into DC. A differentiation circuit 5 is adapted to differentiate the output voltage of the AC-DC transducer 4. A voltage comparison circuit 6 is adapted to generate the output at terminals 7 and 8 when the differentiation output of the differentiation circuit 5 has exceeded a predetermined set value.

As a material for constituting the humidity-sensing resistor 1, electrodes, organic polymers, metallic thin membranes, metal oxides, or the like is provided. According to the examination results by inventors, it has been found out that the metal oxide among the humidity-sensing materials is useful and particularly a metal oxide ceramic humidity-sensing resistor is suitable and optimum where variation in temperature, humidity or air flow is involved, which is considered to be most difficult for the humidity detection.

The metal oxide ceramic humidity-sensing resistor is an element made by metal oxide ceramic materials which are preferred to contain at least one component from among $Cr_2O_3$, $Fe_2O_3$, NiO, ZnO, $SnO_2$, $TiO_2$, $Al_2O_3$, MgO, $In_2O_3$, $MnO_2$, CuO, CoO, $MgCr_2O_4$, $FeCr_2O_4$, $NiCr_2O_4$, $MnCr_2O_4$, $CuCr_2O_4$, $CoCr_2O_4$, $Zn_2TiO_4$, $Zn_2SnO_4$, $Mg_2TiO_4$ and $Mg_2SnO_4$. These metal oxide ceramic materials are thermally stabilized and provided with proper humidity-resistance characteristics across the entire humidity span. In addition, the response property thereof is better as compared with the conventional product. Also, even if contaminants such as oil components or the like are attached on the element surface to change the characteristics, the contaminants can be removed from the element surface through the heating operation of the element. Accordingly, it can always be restored easily to its original characteristics through the application of the heat cleaning operation.

One example of a humidity-sensing resistor 1 is shown in FIG. 2, comprising a metal oxide ceramic element of a plate like shape 11, a pair of electrodes 12, 12 provided on the both sides of the element 11 and a couple of lead wires 13 and 14 each connected to the corresponding electrode 12.

The process for manufacturing the metal oxide ceramic element 11 will be described hereinafter in an embodiment. At first, $Cr_2O_3$, MgO and TiO each being of 99.99% or more in purity were employed as starting materials, and the powders of $Cr_2O_3$, MgO and $TiO_2$ were blended at a composition ratio of 65, 65 and 35 mols, respectively. These material powders were mixed and wet-blended using polyurethane pot with agate balls therein. Then, their mixture was dried and, thereafter, was pressed to form a square plate of $4\times5\times0.25$ $mm^3$ in size under a pressure of 750 $kg/cm^2$. The pressed plate was fired in air for two hours at a temperature of 1,300° C. to obtain a ceramic element, and, then, materials such as $RuO_2$ were baked to provide electrodes, at a temperature of 800° C., on the both major faces of the ceramic element obtained and lead wires made of Pt were connected to the electrodes, respectively. Typical relative humidity-resistance characteristics of humidity-sensing resistor 1 thus obtained are shown in FIG. 3, upon the application within a closed circuit of FIG. 1, wherein a value of the resistor 3 connected to the humidity-sensing resistor 1 was 100 kΩ.

The AC-DC transducer 4 is adapted to obtain the resistance changes of the humidity-sensing resistor 1 within the closed circuit as the voltage changes. The AC-DC transducer can, for instance, be constituted by a circuit, which has an operational amplifier OP, resistors R1, R2 and R3, diodes D1 and D2, and a capacitor C1 as shown in the diagram of FIG. 1(a). When the output of the circuit is not sufficient, an amplification circuit is required to be added to the circuit for amplification of the output.

The differential circuit 5 is adapted to draw out the changed portion from the output of the AC-DC transducer 4. Namely, the differential circuit is adapted to draw out signal components which are larger in time changes, while removing signal components which are smaller in time changes, with employment of the well-known differential circuit. According to the experiments by the inventors, the voltage differential time constant within the range of 0.1 to 20 (seconds) was most practical when the differentiation circuit 5 was composed of a resistor R4 and a capacitor C2, as shown in the diagram of FIG. 1(b). As the value of the differential time constant of the differential circuit 5 becomes smaller, only signals which are larger in time changes can be detected. On the contrary, as the differential time constant value becomes larger, signals which are small in time changes can pass through the system of the circuit. When the value of the voltage differential time constant is not larger than 0.1, noises are likely to be mixed thereinto, since the humidity response property of the humidity-sensing resistor 1 is not faster as compared with that of the differential circuit 5. When the value of the voltage differential time constant becomes not smaller than 20, signals which correspond to not only resistance changes of the humidity-sensing resistor 1 caused due to the humdity leakage from a system where heating steam passes but also slower time change due to drift components such as the ambient temperature and wind direction can be detected by the differential circuit 5. For this reason, it is to be noted that the value of the differential time constant is desirable to be within a range of 0.1 to 20 (seconds) in the case of humidity-leakage detection.

The voltage comparison circuit 6, is constituted by a well-known comparison circuit, i.e., a circuit composed of a voltage comparator VC and a reference voltage source VR, as shown in the diagram of FIG. 1(c). In the voltage comparison circuit 6, it is easy to arrange such that the reference value of the reference voltage source may be changed at need.

With an humidity detecting apparatus as constructed above, assuming that the relative humidity varies around the humidity-sensing resistor 1, the relative humidity variation is detected with the humidity-sensing resistor 1 and the detecting signal thereof is added, as the voltage changes, to the AC-DC transducer 4. The output signal of the AC-DC transducer 4 can be differentiated by the differential circuit 5 to draw out the variations only. The time constant of the differential circuit 5 is made a value within the above-described range to draw out only humidity leakage signals. Then, signals obtained through differential circuit 5 is outputted through detection of signals only, exceeded a desired set value, by the voltage comparison circuit 6. The detection signals of the voltage comparison circuit 6 are obtained between the terminals 7 and 8. The output signal from the terminals 7 and 8 operates the other various controlling appliances or display appliances, indicating instruments, etc. in a known manner.

As one experiment with the use of the above humidity detecting apparatus, a location where steam of 300° C. at temperature is leaking from a hole of 10 μm in diameter could be detected, even under the condition of a 2 meter per second at air velocity, by the inventors.

One example where the humidity detecting apparatus of the present invention has been applied to a microwave oven is shown in FIG. 4. Referring to FIG. 4, a control circuit 9 for a microwave oven 10 is connected to the output terminals 7 and 8 of an apparatus shown in FIG. 1.

Figure 4B:
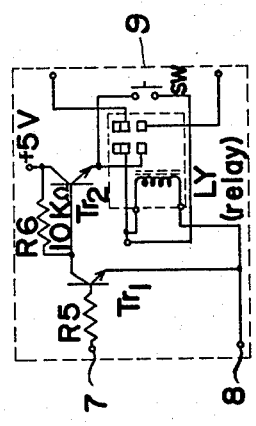

The control circuit 9, which is composed of transistors Tr1, Tr2, resistors R5, R6, a self-retaining type relay Ly and a start switch SW1, as shown in the diagram of FIG. 4(b), turns on and off the current to the magnetron M of the microwave oven 10.

Within the control circuit 9, assuming that the start switch SW1 is closed, the transistor Tr2 is connected to the coil of the relay Ly and is turned on. Current from the transistor Tr2 flows to the coil of the relay Ly to close one of the contacts of the relay Ly and, then the current flows to a magnetron M to oscillate the magnetron M. Simultaneously the other contact of the relay Ly is closed to provide a self-holding circuit, whereby the transistor Tr2 and the coil of the relay Ly remain connected even if the start switch SW1 is turned off, to let the current to continuously flow to the magnetron M. Food F which is placed inside the microwave oven 10 absorbs the microwave waves to cause heat and steam. Thus, the relative humidity inside the microwave oven becomes higher rapidly, and the changing thereof appears as variation in resistance of the humidity-sensing resistor 1. The variation in resistance of the humidity-sensing resistor 1 is detected by the AC-DC transducer 4, the differential circuit 5 and the voltage comparison circuit 6. When the output voltage of the differential circuit 5 exceeds the predetermined set voltage of the voltage comparison circuit 6, the voltage comparison circuit 6 produces the output voltage to the control circuit 9. The transistor Tr1 of the control circuit 9 is turned on through the output voltage of the voltage comparison circuit 6 to turn off the transistor Tr2. Thus, the current flows no more from the transistor Tr2 to the coil of the relay Ly to turn off the contact of the relay Ly, resulting in that the current flow to the magnetron M is suspended. Accordingly, the oscillation operation of the magnetron M is suspended to complete the heating operation of the food F within the microwave oven.

Since the humidity detecting apparatus of the present invention differentiates the variation in a signal obtained by the humidity-sensing resistor as described hereinabove, the humidity detecting apparatus can detect the existence of the humidity leakage, if surrounding conditions vary, by selection of the differential time constant in accordance with the conditions of the using surroundings. Needless to say, the moistening of atmosphere to be measured can be detected by the employment of the humidity apparatus of the present invention. And a metal oxide ceramic is used as the humidity-sensing resistor to stably detect the moisture even at elevated temperatures and to detect the leakage of the high temperature and pressure steam from boilers, steam supply pipes, etc. Also, comparison between the differential circuit and the desired set value by the comparison circuit can indicate whether or not the humidity leakage extent is within the tolerable range in the humidity leakage. Furthermore, the detection can be made as to whether variation in humidity of the atmosphere to be measured is larger than a set value, as mentioned above in such a manner that the humidity detecting apparatus of the present invention can be applied to ovens or the like to automatically cook if the conditions of the surrounding temperature, humidity, wind or the like are varied.

Although the present invention has been described and illustrated in detail, it is to be clearly understood that the same is by way of limitation, the spirit and scope of the present invention being limited only by the terms of the appended claims.

What is claimed is:

1. A humidity detecting apparatus comprising a humidity-sensing resistor and a differential circuit for differentiating the voltage variation accompanied by the resistance variation of the humidity-sensing resistor thereby to detect variations in the surrounding humidity of said humidity-sensing resistor.

2. A humidity detecting apparatus in accordance with claim 1, wherein the humidity-sensing resistor is a metal oxide ceramic humidity-sensing resistor.

3. A humidity detecting apparatus in accordance with claim 1, wherein a metal oxide ceramic humidity-sensing resistor is used as humidity-sensing resistor and the differential constant of the differential circuit is set within the range of 0.1 to 20 (second) to make it possible to detect the humidity leakage.

4. A humidity detecting apparatus in accordance with claim 1 or claim 3, wherein the humidity-sensing resistor is a ceramic, with an electrode attached thereto, of at least one oxide selected from among $Cr_2O_3$, $Fe_2O_3$, $NiO$, $ZnO$, $SnO_2$, $TiO_2$, $Al_2O_3$, $MgO$, $In_2O_3$, $MnO_2$, $CuO$, $CoO$, $MgCr_2O_4$, $FeCr_2O_4$, $NiCr_2O_4$, $MnCr_2O_4$, $CuCr_2O_4$, $CoCr_2O_4$, $Zn_2TiO_4$, $Zn_2$, $SnO_4$, $Mg_2TiO_4$ and $Mg_2SnO_4$.

* * * * *